United States Patent [19]
Chwalisz et al.

[11] Patent Number: 6,040,340
[45] Date of Patent: Mar. 21, 2000

[54] IMPLANTATION RATES AFTER IN VITRO FERTILIZATION, TREATMENT OF INFERTILITY AND EARLY PREGNANCY LOSS WITH A NITRIC OXIDE DONOR ALONE OR IN COMBINATION WITH PROGESTERONE, AND A METHOD FOR CONTRACEPTION WITH NITRIC OXIDE INHIBITORS

[75] Inventors: Krzysztof Chwalisz, Berlin, Germany; Robert E. Garfield, Friendswood, Tex.

[73] Assignees: Schering Aktiengesellschaft, Berlin, Germany; The Board of Regents, Univ. of Texas System, Austin, Tex.

[21] Appl. No.: 08/646,518

[22] Filed: May 7, 1996

[51] Int. Cl.⁷ ..................................... A61K 31/21
[52] U.S. Cl. .......................... 514/509; 514/258; 514/567; 514/307; 514/263; 514/608; 514/565; 424/608
[58] Field of Search .............................. 424/608; 514/509, 514/258, 562, 307, 263, 608, 565

[56] References Cited

U.S. PATENT DOCUMENTS 5,470,847   11/1995   Garfield et al. .......................... 514/121
5,508,045   4/1996   Harrison et al. .......................... 514/509

FOREIGN PATENT DOCUMENTS

WO 95/22345   8/1995   WIPO .

OTHER PUBLICATIONS

Bayhi et al., J. Clin. Anesth., 4:487–488 (1992).
Conrad, FASEB, 7:566–571 (1993).
Diamond, J. of Pharm. & Exp. Thera., 168(1):21–30 (1969).
Garfield et al., "Control of Myometrial Contractility and Labor," Basic Mechanisms Controlling Term and Preterm Labor, Springer–Verlag Berlin, eds. Chwalisz et al. (1994).
Yallampalli et al., Soc. Gynecol. Invest. Abst. P41 (1993).
Greenspoon et al., Lancet, 338:124 (1991).
Izumi et al., Am. J. Obstet. Gynecol., 170:236–245 (1994).
Jennings et al., J. of Mat. Fetal Med., 2:170–175 (1993).
Lees et al., Lancet, 343:1325–1326 (1994).
Natuzzi et al., Biochem. & Biophys. Res. Comm., 194(1):1–8 (1993).
Papka et al., Neuroscience Letters, 147:224–228 (1992).
Ramsey et al., Europ. J. of Clinical Investigation, 24:76–78 (1994).
Sladek et al., Am. J. Obstet. Gynecol., 169:1285–1291 (1993).
Yallampalli et al., Am. J. Obstet. Gynecol., 169:1316–1320 (1993).
Yallampalli et al., Endocrinology, 133(4):1899–1904 (1993).
Yallampalli et al., Am. J. Obstet. Gynecol., 170:175–185 (1993).
Yallampalli et al., Endocrinology, 134(4):1971 (1994).

*Primary Examiner*—Keith D. MacMillan
*Attorney, Agent, or Firm*—Millen, White, Zelano & Branigan, P.C.

[57] ABSTRACT

A method is provided for the improvement of implantation rates and/or pregnancy rates in a female mammal, comprising administering to a female mammal in whom pregnancy is desired an effective amount of (a) a nitric oxide synthase substrate, a nitric oxide donor, or both, optionally in combination with (b) a progestin, and, (c) optionally, in further combination with an estrogen.

A method is also provided for fertility control for a female mammal, comprising administering to a female mammal in whom pregnancy is not desired and at risk for becoming pregnant an effective amount of nitric oxide synthase inhibitor in combination with an antiprogestin. Pharmaceutical compositions are also provided.

27 Claims, 6 Drawing Sheets

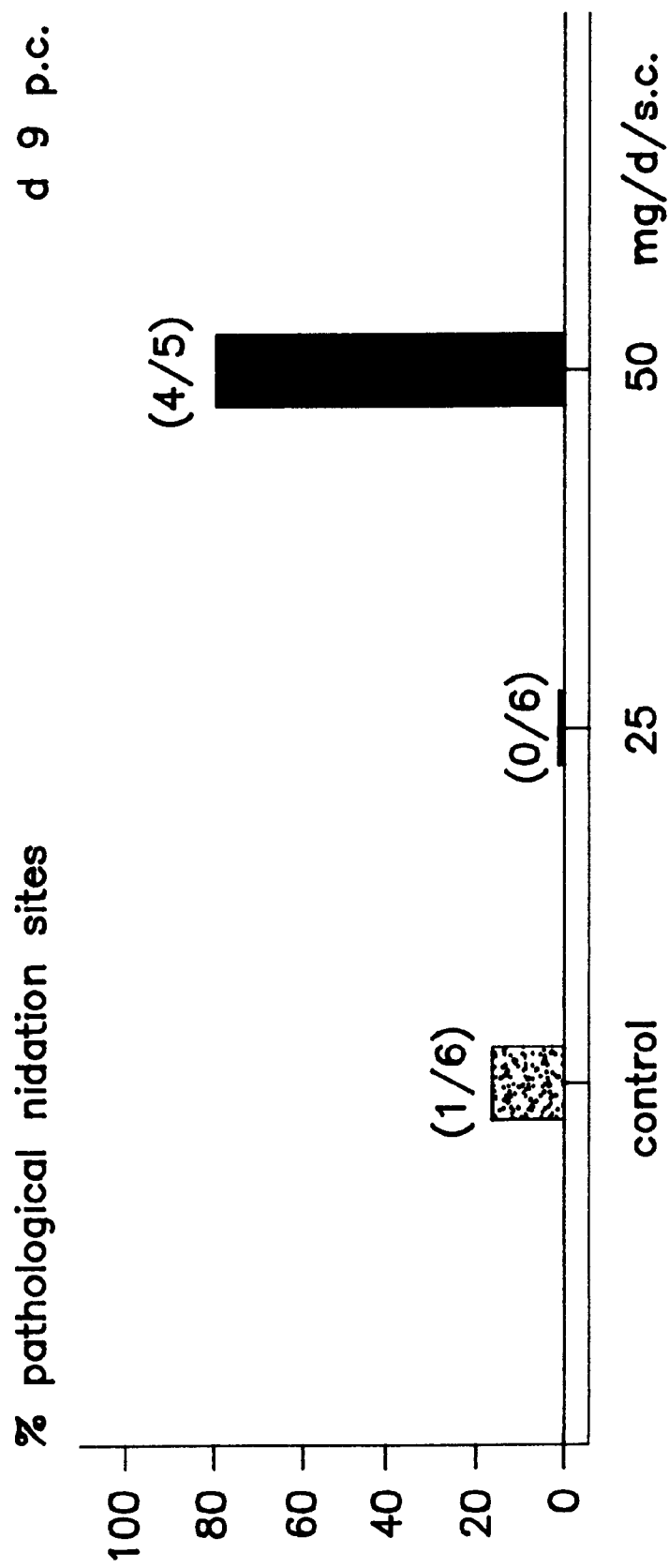
FIG. IA

IMPLANTATION RATES AFTER IN VITRO FERTILIZATION, TREATMENT OF INFERTILITY AND EARLY PREGNANCY LOSS WITH A NITRIC OXIDE DONOR ALONE OR IN COMBINATION WITH PROGESTERONE, AND A METHOD FOR CONTRACEPTION WITH NITRIC OXIDE INHIBITORS

BACKGROUND OF THE INVENTION

This invention relates to a method for the improvement of implantation rates after in vitro fertilization (IVF), for the treatment of infertility and for the treatment and prevention of early pregnancy loss in women with a nitric oxide synthase substrate (L-arginine), a nitric oxide donor or both, alone or in combination with progesterone and/or estrogen.

Human in vitro fertilization is surprisingly unsuccessful. The overall birth rate per IVF treatment cycle is approximately 14% in USA (Medical Research International Society for Assisted Reproductive Technology [SART], The American Fertility Society [1992]. Fertil Steril 5:15 ), and 12.5% in UK (The Human Fertilization and Embryology Authority. Annual Report, London 1992).

Success is greater when more than one embryo is transferred simultaneously. However, simultaneous transfer of multiple embryos increases the incidence of multiple pregnancy and the possibility of miscarriage and prematurity. The reasons for the low pregnancy rates after IVF are still not completely understood. The quality of both the embryo and the uterine environment affects success. Generally, there is a high rate of spontaneous early abortion in fertile cycles in women. After natural conception, possibly as many as 50–60% of very early pregnancies are lost (Winston M L, Handyside A H [1993], New challenges in human in vitro fertilization. Science 260:932–935). This may be due to both conceptus abnormalities and dysynchrony between embryo and endometrium at the time of embryo transfer.

Most losses may be due to abnormalities of the conceptus or the still inappropriate culture conditions, since the success of embryo transfer after IVF decreases as the time after insemination increases (Winston M L, Handyside A H [1993], New challenges in human in vitro fertilization. Science 260:932–935).

To overcome possible deficiencies in culture media, transfer of oocytes (gamete intrafallopian transfer—GIFT) or zygotes directly to the fallopian tube (zygote intrafallopian transfer—ZIFT) has been performed in women with intact oviducts. However, these attempts only slightly increased the fertility and birth rates after IVF (Edwards R G [1995] Clinical approaches to increasing uterine receptivity during human implantation. Hum Reprod 10, Suppl 3:60–67).

The effect of uterine environment on fertility rates after IVF may be equally important. It has been well established that the successful establishment of pregnancy after embryo transfer requires both a healthy blastocyct and a receptive uterus. Embryo transferred to an inadequately primed uterus are unlikely to implant. In all mammals, the endometrium, is receptive for implantation only during the specific period of time after ovulation. This phase of the luteal phase is called "implantation window". In women, the successful implantation may only take place between days 15–20 of a histologically defined 28-day cycle, i.e. during the period of highest progesterone levels (Navot D, Scott R T, Droesch K D, Veeck L L, Hung-Ching Liu, Rosenvaks Z [1991], The window of embryo transfer and efficiency of human conception in vitro. Fertil Steril 55:114–118). The optimum condition for implantation was estimated on days 20–22 of the normal cycle, i.e. 7 days after the LH surge (Bergh P A, Navot D [1992], The impact of embryonic development and endometrial maturity on the timing of implantation. Fertil Steril 58:537–542).

Adequate progesterone priming of the endometrium is essential for a successful implantation, and treatment with an antiprogestin during the luteal phase will completely prevent implantation (Chwalisz K, Stöckemann K, Fuhrmann U, Fritzemeier K H, Einspanier A, Garfield R E [1995] Mechanism of action of antiprogestins in the pregnant uterus. In Henderson D, Philibert D, Roy A K, Teutsch G (eds) Steroid Receptors and Antihormones. Ann N. Y. Acad Sci 761:202–224). In the fertile cycle, progesterone regulates the transport of the fertilized egg through the oviduct and induces secretory changes required for implantation in the endometrium. Implantation is a precisely timed event in mammals. The secretory endometrial proteins (Beier H M, Elger W, Hegele-Hartung C, Mootz U, Beier-Hellwig K [1992] Dissociation of corpus luteum, endometrium and blastocyst in human implantation research. J Reprod Fert 92:511–523), and probably other intracellular and cell surface proteins, such as integrins, cytokines and growth factors produced by endometrial epithelial cells as a result of progesterone stimulation, are necessary for implantation to take place (Edwards R G [1995] Physiological and molecular aspects of human implantation. Hum Reprod 10, Suppl 2:1–14).

The asynchrony between embryo and endometrial development has been previously recognized as one of possible causes of implantation failures after IVF (Beier H M, Elger W, Hegele-Hartung C, Mootz U, Beier-Hellwig K [1992] Dissociation of corpus luteum, endometrium and blastocyst in human implantation research. J Reprod Fert 92:511–523). However, no effective methods to increase the implantation rates are available to date. The most advanced stages of human implantation are chracterized by the invasion of trophoblastic cells into the decidua and angiogenesis (Loke Y W, King A [1995] Human Implantation. Cell biology and immunology. Cambridge University Press). This stages are also dependent on progesterone, since progesterone antagonists also disrupt early pregnancy (Chwalisz K, Stöckemann K, Fuhrmann U, Fritzemeier K H, Einspanier A, Garfield R E [1995] Mechanism of action of antiprogestins in the pregnant uterus. In Henderson D, Philibert D, Roy A K, Teutsch G (eds) Steroid Receptors and Antihormones. Ann N. Y. Acad Sci 761:202–224). During early pregnancy, an adequate blood flow to the uterus is essential for embryo development. An impaired blood flow to the uterus can jeopardize the establishment of pregnancy (Edwards R G (1995) Clinical approaches to increasing uterine receptivity during human implantation. Hum Reprod 10, Suppl 3:60–67). Patients with an impeded blood flow have been given aspirin to improve their blood flow. Low dose aspirin is thought to increase the prostacyclin to thromboxane A2 ratio and thereby to increase placental perfusion. However; the aspirin effect on uterine blood flow were only marginal (Goswamy R K, Williams G, Steptoe P C [1988], Decreased uterine perfusion- a cause of infertility. Hum. Reprod 3955–959; Wada I, Hsu C C; Williams G, Macnamee M C, Brinsden P R [1994], The benefits of low-dose-aspirin therapy in women with impaired uterine perfusion during assisted conception. Hum Reprod 9:1954–1957).

One of the most exciting recent advances in biology and medicine is the discovery that nitric oxide is produced by endothelial cells and that its is involved in the regulation of vascular tone, platelet aggregation, neurotransmission and immune activation. Nitric oxide is an important mediator of relaxation of the muscular smooth muscle and was formerly known as EDRF (endothelin-derived relaxing factor) (Furchgott R F and Zawadzki J V [1980], *The obligatory role of endothelial cells in the relaxation of arterial smooth muscle by acetylcholine. Nature* 288:373–376; Moncada S, Palmer R M G and Higgs E A [1991], *Nitric oxide; physiology, pathophysiology and pharmacology. Pharmacol Rev* 43:109–14. Nitric oxide is synthesized by the oxidative deamination of a guanidino nitrogen of L-arginine by at least three different isoforms of a flavin-containing enzyme, nitric oxide synthase (Moncada S, Palmer R M G and Higgs E A [1991], *Nitric oxide; physiology, pathophysiology and pharmacology. Pharmacol Rev* 43:109–144. Synthesis of nitric oxide has been shown to be competitively inhibited by analogues of L-arginine; NG-nitro-L-arginine methyl ester (L-NAME), NG-monoethyl-L-arginine (LMMA), N-iminoethyl-L-arnithine (L-NIO), L-monomethyl-L-arginine (L-NNMA) and L-NG-methylarginine (LNMA) and Nw-nitro-L-arginine (L-NA).

Nitric oxide elevates levels of cGMP (1,4,5-cyclic guanosine monophosphate) within the vascular smooth muscle to produce relaxation and to reduce blood vessels tone (Moncada S, Palmer R M G and Higgs E A. [1991], *Nitric oxide; physiology, pathophysiology and pharmacology. Pharmacol Rev* 43:109–142). *Nitric oxide binds to heme and thus activates soluble guanylate cyclase* (Ignarro L J [1991], *Physiological significance of Nitric oxide. Seminars in Perinatology* 15:20–26) to increase the cellular content of cGMP. It has long been recognized that nitrovasodilators, such as sodium nitroprusside and nitroglycerin, inhibit vascular smooth muscle contractility to produce relaxation or to reduce vascular tone. These agents have been used since the late 1980s as vasodilators. However, only recently has the mechanism of action of these compounds been realized. Nitrovasodilators are now classified as nitric oxide donors because they are metabolized or spontaneously release nitric oxide (Moncada S, Palmer R M G and Higgs E A. [1991], *Nitric oxide; physiology, pathophysiology and pharmacology. Pharmacol Rev* 43:109–142). The long-used nitrovasodilators may be regarded as substitution therapy for a failing physiological mechanism. Nitric oxide is also produced by macrophages and other immune cells.

Three highly related NOS enzymes have been isolated and identified. These Include endothelial NOS (e-NOS, type III), neuronal NOS (n-NOS, type II) and inducible NOS (i-NOS, type I) (Knowles R G and Moncada S [1994], *Nitric oxide synthases in mammals. Biochem J* 298:249–258; Sessa W C. [1994], *The Nitric Oxide Synthase Family of Proteins. J Vasc Res* 1994; 31:131–143; Nathan C [1992], *Nitric oxide as a secretory product of mammalian cells. FASEB J* 6:301–3064). The constitutive isoforms e-NOS and b-NOS were originally identified in endothelial and neuronal tissues, respectively, and they rapidly and transiently produce small amounts of NO under basal conditions. The i-NOS isoform is inducible by cytokines or endotoxin (LPS) and it produces large quantities of NO for hours or days in a $Ca^{2+}$-independent manner. Cells expressing iNOS do not generate NO under basal conditions. The e-NOS form of the enzyme is expressed in endothelial cells, in cardiac myocytes, platelets and some neurones. The e-NOS-derived NO is the most important vasodilator. It is released In low levels to maintain a constant vasorelaxation and maintain normal blood pressure. The n-NOS isoform is thought to act as a neurotransmitter. It is thought to be important in mediating such functions as gastrointestinal motility and penile erection.

There is a substantial body of evidence from animal experiments that a deficiency in nitric oxide contributes to the pathogenesis of a number of diseases, including hypertension, atherosclerosis and diabetes (Moncada S, Palmer R M G and Higgs E A [1991], *Nitric oxide; physiology, pathophysiology and pharmacology. Pharmacol Rev* 43:109–142). There are many recent studies showing that the inhibition of nitric oxide synthase dramatically increases blood pressure. Treatment of pregnant rats and guinea pigs with nitric oxide synthase inhibitors produce symptoms identical to preeclampsia (Chwalisz K and Garfield R E [1994], *Role of progesterone during pregnancy: Models of parturition and preeclampsia. Z. Geburtsh. u. Perinat.* 198:170–180). Preeclampsia is characterized by increased blood pressure and peripheral vascular resistance, fetal growth retardation, proteinuria and edema. In humans, histopathologic and clinical (fetal growth retardation, fetal death) evidence indicate that reduced placental perfusion is the earliest and most consistent change observed in preeclampsia (Roberts J M and Redman C W G. [1993], *Pre-eclampsia: more than pregnancy-induced hypertension* 341:1447–1451; Friedman E A 1988], *Preeclampsia: a review of the role of prostaglandins. Obstet Gynecol* 71:122–137).

The L-arginine-NO system is present in the uterus (Garfield R E and Yallampalli C. [1993] *Control of myometrial contractility and labor. In: Basic Mechanisms Controlling Term and Preterm Birth.* ed: K Chwalisz, R E Garfield, Springer-Verlag, New York, pp. 1–29; Chwalisz K and Garfield R E. [1994], *Antiprogestins in the Induction of labor. Ann New York Acad Scie* 734:387–413; Buhimschi I, Yallampalli C, Dong Y-L and Garfield R E. [1995], *Involvement of a nitric oxide-cyclic guanosine monophosphate pathway in control of human uterine contractility during pregnancy. Am J Obstet Gynecol* 172:1577–1584; Sladek S M, Regenstrin A C, Lykins D. et al. [1993], *Nitric oxide synthase activity in pregnant rabbit uterus decreases on the last day of pregnancy. Am J Obstet Gynecol* 169:1285–1291). This system plays an important role in control of uterine contractility, pregnancy maintenance, onset of labor and also fetal perfusion. L-arginine and nitric acid caused a rapid and substantial relaxation of spontaneous activity of the uterine strips from rats at mid to near term gestation (Buhimschi I, Yallampalli C, Dong Y-L and Garfield R E [1995] *Involvement of a nitric oxide-cyclic guanosine monophosphate pathway in control of human uterine contractility during pregnancy. Am J Obstet Gynecol* 172:1577–1584; Garfield R E and Yallampalli C. [1993] *Control of myometrial contractility and labor. In: Basic Mechanisms Controlling Term and Preterm Birth.* ed: K. Chwalisz, R E Garfield, Springer-Verlag, New York, pp. 1–29; Sladek S M, Regenstrin A C, Lykins D. et al. [1993] *Nitric oxide synthase activity in pregnant rabbit uterus decreases on the last day of pregnancy. Am J Obstet Gynecol* 169:1285–1291; Natuzzi E S, Ursell P C, Harrison M. et al [1993], *Nitric oxide synthase activity in the pregnant uterus decreases at parturition. Biochem Biophys Res Commun* 194:108–114; Jennings R W, MacGillvray T E and Harrison M R. [1995], *Nitric oxide inhibits preterm labor in the rhesus monkey. J Mat Fet Med* 2:170–175).

The expression of NOS enzymes in the rat uterus was studied with immunoblotting with monoclonal antibodies, i-NOS and e-NOS were detected in the uterus (myometrium) The uterine i-NOS enzyme decreased in the uterus during labor at term and preterm in animals treated to deliver prematurely. Opposite changes were observed in the cervix (Buhimschi I, Ali M, Jain V, Chwalisz K and Garfield R E.

[1996], *Differential regulation of nitric oxide in the uterus and cervix during pregnancy and labor. Human Reproduction* [in press]).

NOS is also present in placental tissues and uterine arteries. The trophoblast invasion of uteroplacental arteries in relation to the NO synthase isoform expression was studied in pregnant guinea pigs by means of immune- and histochemistry as compared to arterial dilatation. A pronounced dilatation of uteroplacental arteries begins at mid-pregnancy and progresses until term (Nanaev A, Chwalisz K, Frank H-G, Kohnen G, Hartung C-H and Kaufmann P. [1995], *Physiological dilation of uteroplacental arteries in the guinea pig depends upon nitric oxide synthase activity of extravillous prophoblast. Cell Tissue Res:*282:407–421). This study demonstrates that dilatation of uteroplacental arteries can be seen when Invading trophoblast cells coexpressing endothelial (e-NOS) and macrophage (iNOS) nitric oxide synthase are found in the vicinity of the vessels, i.e. prior to trophoblast invasion of the arterial walls. Conrad et al.,(1993), localized NOS to the syncythiotrophoblast cell layer in human placenta (Conrad K P, Vill M, Mcguire P G, Dail W G, Davis A K [1993], *Expression of nitric oxide synthase by syncythiotrophoblast in human placental villi, FASEB J* 7:1269–1276). Morris et al., (1993), demonstrated both calcium-dependent and calcium-independent activity in human placental villi and the basal plate (Morris N H, Sooranna S R, Eaton B M, Steer P J (1993) *NO synthase activity in placental bed and tissues from normotensive pregnant women. Lancet* 342:679–680), and Myatt et al (1993), showed that placental villous tree synthesized a calcium-dependent-isoform of the NOS (Myatt L, Brockman D E, Langdon G, Pollock J S [1993], *Constitutive calcium-dependent isoform of nitric oxide synthase in the human placenta villous vascular tree. Placenta* 14:373–383; Myatt L, Brockman D E, Eis A L, Pollock J S [1993] *Immunohistochemical Iolalization of nitric oxide synthase in the human placenta. Placenta* 14:487–495). In addition, Buttery et al., (1994) showed that endothelial NOS at term was localized in the endothelium of umbilical artery and vein and in the placental syncythiotrophoblast (Buttery L D K, McCarthy A, Springall A et al., [1994], *Endothelial nitric oxide synthase in the human placenta: regional distribution and proposed regulatory role at feto-maternal interface. Placenta* 15:257–267). Furthermore, Moorhead et al., (1995) have shown that NADPH diaphorase (non-specific reaction to identify nitric oxide synthase) was in various uterine components during early pregnancy (Moorhead C S, Lawhun M, Nieder G L [1995], *Localization of NADPH diaphorase in the mouse uterus during the first half of pregnancy and during an artificially-induced decidual cell reaction. J Histochem Cytochem* 43:1053–1060). Finally, Toth et al., (1995) demonstrated that NOS activity was present in the first trimester human placental homogenates (Toth M, Kukor Z, Romero R,. Hertelendy F [1995], *Nitric oxide synthase in first trimester human placenta: Characterization and subcellular distribution. Hypertens Pregnancy* 14/3:287–300).

These studies suggest that nitric oxide is an important factor regulating placental blood flow and myometrial quiescence during pregnancy. However, there are no studies published to date which demonstrate the detrimental effects of NOS inhibition on implantation or the beneficial effects of nitric oxide donors or substrates on implantation after IVF or in women with early pregnancy loss. In contrast, Haddad et al., (1995) suggested that the increased nitric oxide production is associated with early embryo loss in mice and that iNOS inhibitors can by used to treat early abortion (Haddad E K, Duclos A J, Baines M G [1995], *Early embryo loss is associated with local production of nitric oxide by decidual mononuclear cells. J Exp Med* 182:1143–51).

OBJECTS OF THE INVENTION

It is an object of the invention to provide a method for the improvement of implantation rates after IVF comprising administering a nitric oxide and/or donor in mammals.

It Is another object of the invention to provide a method for treatment and prevention of infertility or early pregnancy loss comprising administering a nitric oxide substrate and/or donor in early pregnant mammals.

It is a further object of the invention to provide a method for improvement of implantation and treatment and prevention of infertility or early pregnancy loss comprising administering a nitric oxide substrate and/or donor in which progesterone or a progestagenic agent in combination with a nitric oxide substrate and/or donor is used.

It is another object of this invention to provide a method in which a progestational agent and an estrogenic agent are administered combination with a nitric oxide substrate and/ or nitric oxide donor for the for Improvement of implantation and treatment and prevention of infertility or early pregnancy loss female mammals.

It Is another object of this invention to provide a method for fertility control comprising administering antiprogestin (e.g. mifepristone, ORG 31710, ORG 33 628, J867, CDB 2914, ZK 137316) and/or progesterone synthase Inhibitor (e.g. epostane, trilostane) in combination with an nitric oxide synthase inhibitor.

A further object is the provision of pharmaceutical compositions useful in practicing the methods of this invention. Upon further study of the specification and appended claims, further objects and advantages of this invention will become apparent to those skilled in the art.

SUMMARY OF THE INVENTION

In a method aspect, this invention relates to a method of improving implantation rates after IVF or treating of early pregnancy loss which comprises administering to an individual manifesting the symptoms thereof one or both of a nitric oxide substrate and a nitric oxide donor, alone or in combination with progesterone alone or in further combination of an estrogen, in amounts effective to ameliorate the symptoms thereof, the amount of the nitric oxide synthase substrate and nitric oxide donor or both being effective to increase implantation and birth rates by raising the blood level of circulating L-arginine in a female to whom the composition is administered to at least 10 to 500 μmole above the normally 50–1000 μmole circulating levels or raise nitric oxide donor levels to about 10 nM to 100 μM (micromolar), the amount of the progestational agent administered being bioequlvalent to 10–300 mg of injected progesterone, and the amount of the estrogen being bioequlvalent to approximately 2 mg per day of estradiol (Progynova$^R$, Schering).

In a method aspect, this invention relates to a method of fertility control which comprises administering to a female mammal a nitric oxide inhibitor and an antiprogestin, alone or in combination with a progesterone synthase inhibitor. In one embodiment, this fertility control is effected prior to implantation.

In a product aspect, this invention relates to a pharmaceutical composition comprising at least one of a nitric oxide synthase substrate (L-arginine) and a nitric oxide donor (e.g.

sodium nitroprusside or glyceryl trinitrate), alone or in further combination with one or more of a progesterone/progestin and/or estradiol/estrogen with the amount of the nitric oxide synthase substrate, a nitric oxide donor or both per unit dosage being equivalent to either raise the blood level of circulating L-arginine to least 10 to 500 µM above the normally 50 to 1000 µM circulating level or raise nitric oxide donor levels to about 10 nM to 100 µM, the amount of the estrogen being bioequivalent to about 2 mg of estradiol (e.g. Progynova$^R$, Schering) with the amount of the progesterone bioequivalent to 5 to 300 mg of injected progesterone.

In a product aspect, this invention relates to a pharmaceutical composition comprising at least one of a nitric oxide synthase inhibitor in combination with an antiprogestin alone or/and in further combination with a progesterone synthase inhibitor.

DETAIL DISCLOSURE

The methods of this invention improve the implantation and birth rates after IVF and treat early pregnancy loss in pregnant female, who is manifesting the symptoms thereof.

Because the low implantation and birth rates and early pregnancy loss are produced by or aggravated by inadequate uterine blood supply to the conceptus due to insufficient or subnormal nitric oxide synthesis, both nitric oxide synthase substrates, e.g., L-arginine and nitric oxide donors, e.g., sodium nitroprusside, nitroglycerin, glyceryl trinitrate, SIN-1, isosorbid mononitrate, isosorbid dinitrate and diethylenetriamine/NO (DETA/NO), are useful for ameliorating the symptoms thereof and, in one respect of this method of this invention, a combination of both are employed.

An additive effect is achieved when a progestagenic and/or and estrogenic agent is administered concurrently with a nitric oxide substrate and/or nitric oxide donor. In the case of a female mammal, a progestagenic agent can be administered concurrently with or in lieu of an estrogen.

Thus, the method aspect of this invention and the pharmaceutical composition aspect of this invention employs either or both of a nitric oxide substrate and a nitric oxide donor and, optionally one or more of an estrogen (e.g., Progynova$^R$, Schering) or a progestin (e.g. progesterone or hydroxyprogesterone caproate [Proluton$^R$ Depot], etc.).

Examples of dosage ranges of typical NO-substrates and NO-donors (per os) are:

|  | total dose: |
| --- | --- |
| L-Arginine | 500 mg - 10 g p. o. |
| Sodium nitroprusside | 500–2000 µg/kg/day |
| Nitroglycerin | 0.5–10 mg |
| Isosorbid mononitrate | 10–100 mg |
| Isosorbid dinitrate | 10–100 mg |

Examples of combinations of active agents which can administered concurrently with a nitric oxide substrate and/or nitric oxide donor are the following estrogens and progestins and typical oral dosage ranges active agents of the estrogen and progestin with the nitric oxide substrate or donor.

Estrogens: A daily dose bioequivalent to about 1 to 2 mg per day, e.g., Premarin$^R$, Wyeth-Ayerst, 0.625 mg/day, estradiol 25–100 µg/day transdermally or vaginal estradiol gels or creams.

Progestins: A daily dose bioequivalent to 50–300 mg of progesterone/day, e.g., hydroxyprogesterone caproate i.m. to provide a weekly dose of thereof of 100–1000 mg or tablets or dragees providing an effective oral dose of micronized progesterone, or vaginal gel of progesterone in a daily dose of 2–300 mg/day.

Examples of progestins are listed below

| Product | Composition | Dose |
| --- | --- | --- |
| ProlutonR Depot (Schering) | Hydroxyprogesterone caproate | 250–1000 mg/week i.m. |
| Progesteron-Depot (Jenapharm) | Hydroxyprogesterone caproate | 250–1000 mg/week i.m. |

Examples of estrogens are listed below:

| Product | Composition | Dose (mg per day) |
| --- | --- | --- |
| Climaval (Sandoz) | Estradiol valerate | 0.5–4 mg |
| Progynova (Schering) | Estradiol valerate | 0.5–4 mg |

Examples of Antiprogestins are Listed Below:

11β-[4-N,N-(dimethylamino)phenyl]-17α-hydroxy-17β-(3-hydroxypropyl)-13α-methyl-4,9(10)-gonadien-3-one, 11β-(4-acetylphenyl)-17β-hydroxy-17α-(3-hydroxyprop-1 (Z)-enyl)-4,9(10)-estradien-3-one (EP-A 0 190 759), 11β, 19-[4-(cyanphenyl)-o-phenylen]-17b-hydroxy-17α-(3-hydroxyprop-1(Z)-enyl)-4-androsten 3-one (WO-A 93/23020)

11β, 19-[4-(3-pyridinyl)-o-phenylen]-17β-hydroxy-17α-(3-hydroxyprop-1(Z)-enyl)-4-androsten 3-one (WO-A 93/23020).

The invention relates to the discovery that an NO-regulatory system is involved in controlling the success of implantation of a conceptus in the endometrium. Thus, the invention relates to a method of enhancing initiation of successful implantation of a conceptus, as well as enhancing the maintenance of implantation, by administering a nitric oxide synthase substrate or a nitric oxide donor, or both. The invention also relates to a method of inhibiting the initiation of implantation of a conceptus, as well as inhibiting the maintenance of implantation, by administering a nitric oxide synthase inhibitor. These compounds can be administered before or after coitus and/or before or after implantation of the conceptus. Depending on the end result desired, various additional agents can be optionally also administered, as discussed herein. The invention thus relates to methods of affecting the success of implantations in early pregnancy. By early pregnancy is meant, e.g., typically up to about the end of the first trimester of pregnancy.

The pharmacologically active agents employed in this invention can be administered in admixture with conventional excipients, I.e., pharmaceutically acceptable liquid, semi-liquid or solid organic or inorganic carriers suitable, e.g., for parental or enteral application and which do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hycroxy methylcellulose, polyvinyl pyrrolidone, etc.

The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parental application, particularly suitable are solutions, preferably oily or aqueous solutions, as well as suspensions, emulsions, or implants, including suppositories, transdermal patches, and vaginal gels, creams and foams. Ampoules are convenient unit dosages.

In a preferred aspect, the composition of this invention is adapted for ingestion.

For enteral application, particularly suitable are unit dosage forms, e.g., tablets, dragees or capsules having talc and/or carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, Inter alia, tablets, dragees, capsules, pills, granules, suspensions and solutions. Each unit dose, e.g., each table spoon of liquid or each tablet, or dragee contains, for example, 5–5000 mg of each active agent.

Suitable for transdermal application are inter alia transdermal patches and gels.

Solutions for parenteral administration contain, for example, 0.01–1% of each active agent in an aqueous or alcoholic solution.

The nitric oxide substrate and/or donor can be administered as an admixture with an estrogen and/or progestational agent and any other optional active agent or as a separate unit dosage form, either simultaneously therewith or at different times during the day from each other.

The combination of active agents is preferably administered at least once daily (unless administered in a dosage form which delivers the active agents continuously) and more preferably several times daily, e.g., in 2 to 6 divided doses. The typical dose is about 0.5 to 1000 mg of each active agent, although some less active agents, e.g., L-arginine, require much higher oral dosages, e.g., 500 to 10,000 mg, and others, e.g., sodium nitroprusside, require lower doses, e.g., 500–2,000 $\mu$g/kg/day. Doses for nitroglycerine typically are orally 2.6 mg 2× daily; sublingually, 0.8 mg 1–4× daily; and transdermally, 0.2–0.5 mg/hr. The preferred administration form is a transdermal application. Since the LD50 dosages of most of these active agents is known in the prior art, a lower dosage regimen can be initiated and the dosage increased until a positive effect is achieved or a higher dosage regimen can initially be employed, e.g., in a crisis situation, and the dosages regulated downward as relief from the symptoms is achieved. Combinations of agents can be employed either continuously or sequentially.

In humans, both L-arginine and progesterone (or bioequivalent of another progestin) should be given in a ratio which produces blood plasma levels of 50–5000 $\mu$molar L-arginine, 10–100 nmolar estradiol and 100 to 1000 nmolar of progesterone.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 shows the effects of L-NAME (NOS inhibitor) on implantation in rats. The animals were treated with 25 and 50 mg/animal/day L-NAME administered via continuous s.c. infusion from day 1 post coitum (p.c.) until day 7 p.c The autopsy was performed on Either day 9 FIG. 1A, or 12 (FIG. 1B) p.c. and the diameter of the implantation sites were measured (FIG. 1C).

FIG. 2 shows the effects of L-NAME (NOS inhibitor) on implantation in rats. The animals were treated with 25 and 50 mg/animal/day L-NAME administered via continuous s.c. infusion on day 5–7 (p.c.). The autopsy was performed on p.c. and the number of pathological implantation sites were counted (FIG. 2A), and their diameter (FIG. 2B) and weight (FIG. 2C) measured day 12 p.c.

DETAILED DESCRIPTION

Figure 1B:
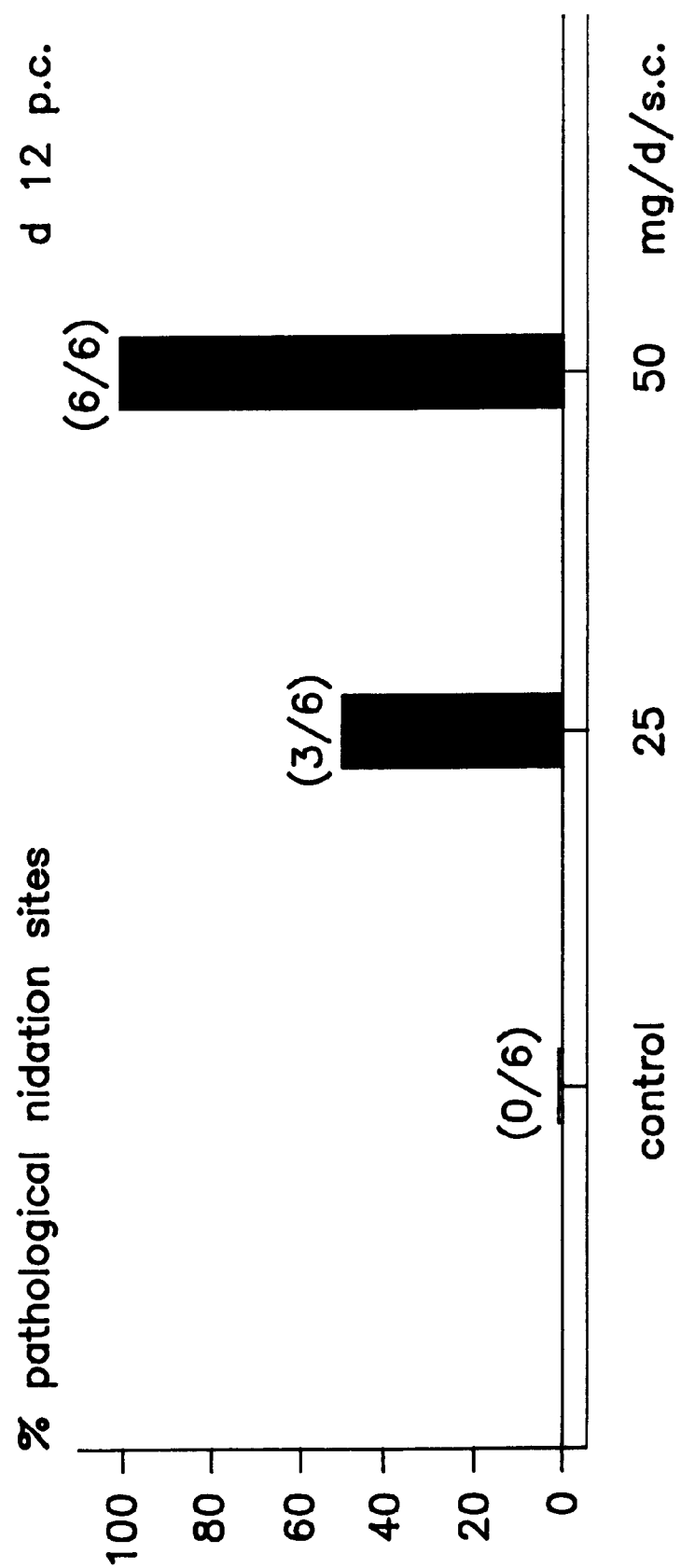
FIG. 1.
Figure 1C:
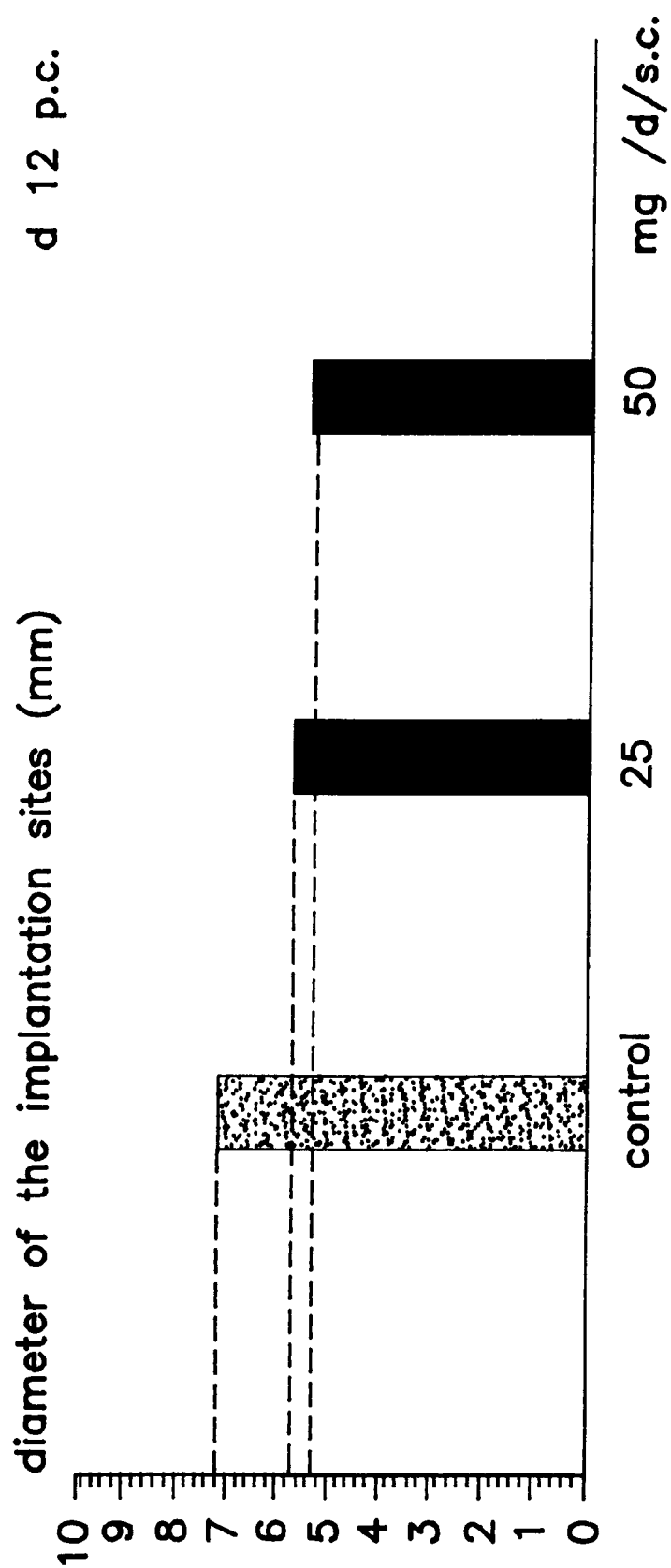
Figure 2A:
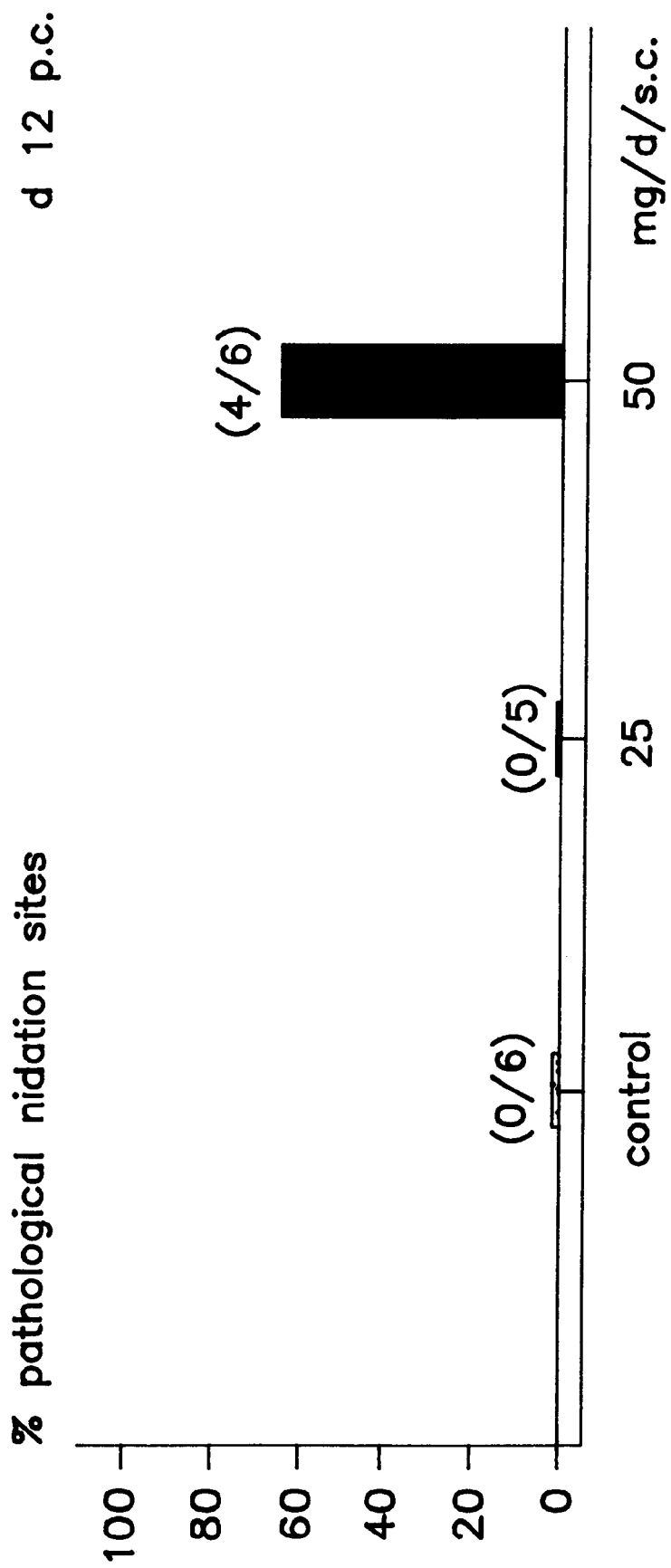
FIG. 2.
Figure 2B:
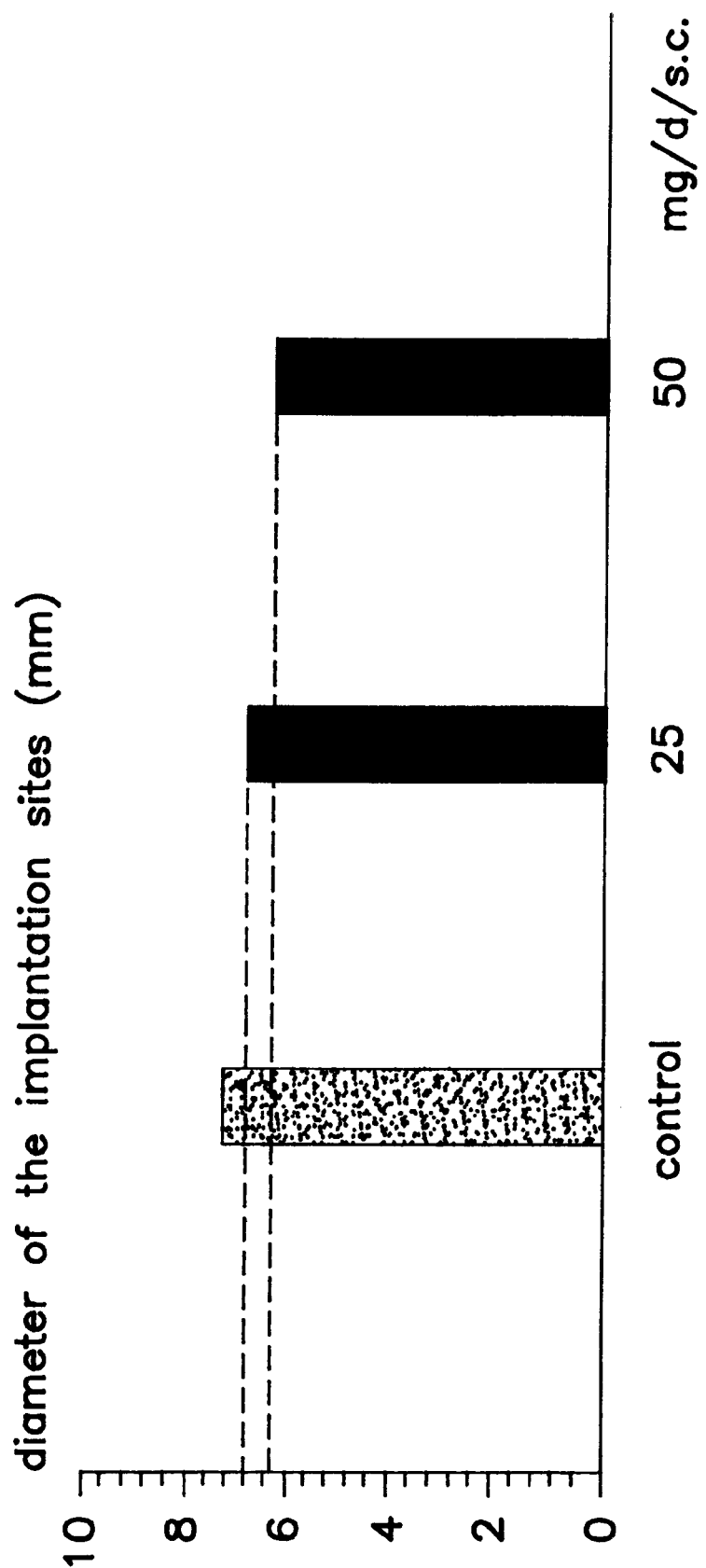
Figure 2C:
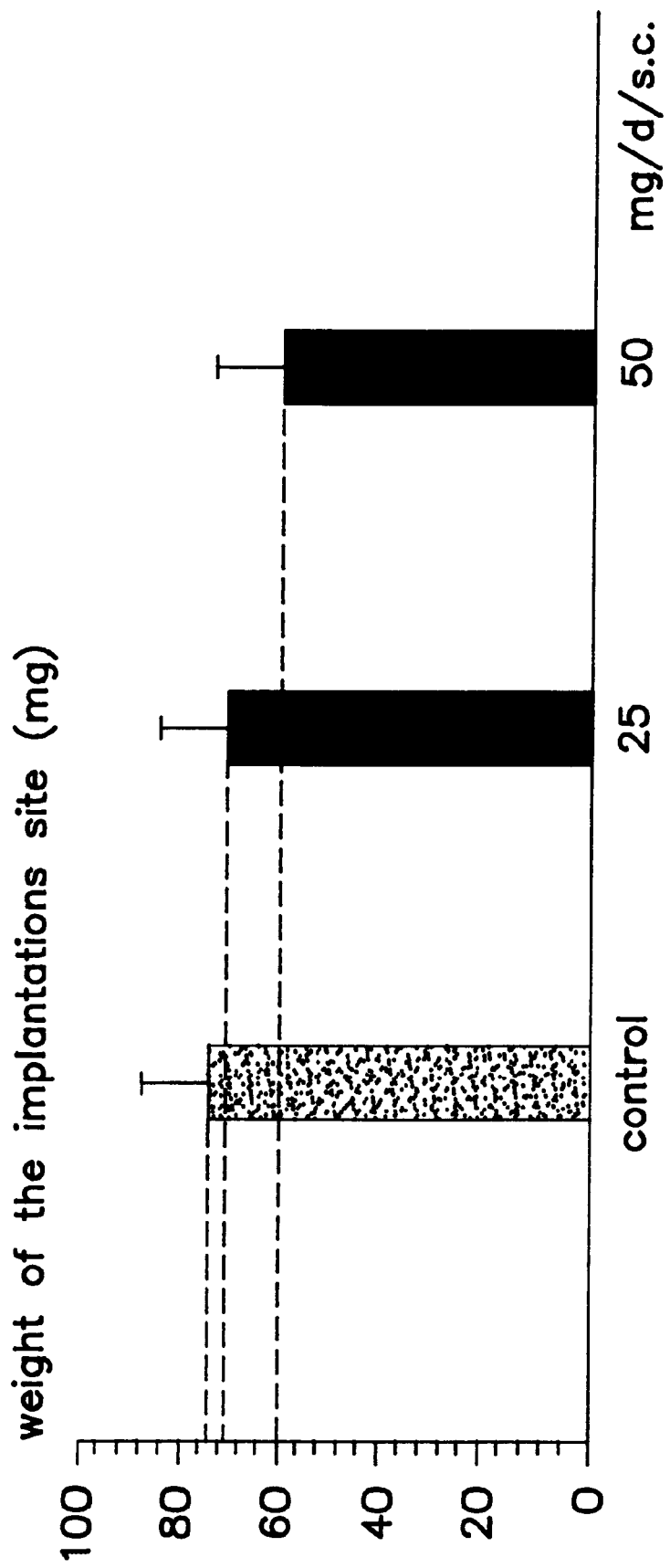

In the experiments whose results are shown in FIG. 1, pregnant rats (n=6/group) were treated with 25 and 50 mg/animal/day L-NAME from day 1 p.c. until day 7 p.c., I.e. during the period of pre-implantation and early implantation (in rats implantation takes place on day 5 p.c. ). The control animals were treated with the vehicle. During autopsy (days 9 and 12 p.c.) the implantation sites were assessed macroscopically, their diameter was measured, and the weights of isolated implantation sites (embryonic and placental tissues) were recorded. FIG. 2 presents results from a second study in pregnant rats in which L-NAME (25 and 50 mg/anilal/day) treatment was performed on days 5–7 p.c., i.e. shortly after nidation had taken place. The autopsy was performed on day 12 p.c.. Implantation showing haemorrhagic changes were defined as pathological implantation sites.

It can be concluded from these results that the nitric oxide synthase inhibitor L-NAME has a profound effect on implantation. There was a dose-dependent inhibition of the size and weigh of the implantation sites. In addition, L-NAME induced pathological changes in the implantation sites (mainly haemorrhages). Furthermore, other studies have demonstrated that the L-NAME-induced effects on implantation were enhanced with low-dose (0.1–0.3 mg/animal/day) treatment with the antiprogestin onapristone.

The results of these studies indicate that nitric oxide plays a pivotal role during implantation. It seems to be important for placental perfusion during the entire implantation process. Nitric oxide deficiency in the uterus can lead to either resorption of implantation sites or to spontaneous abortions. Therefore, nitric oxide donors or substrates alone or in combination with a steroid hormones (progesterone estradiol) will prove effective for improvement of implantation rates and treatment of infertility and early pregnancy loss. Furthermore, a combination of nitric oxide inhibitors with antiprogestins will be effective in preventing or interrupting pregnancy.

EXAMPLE

Example 1

Improvement of implantation rates after in vitro fertilization with a nitric oxide substrate. To a human female (50–90 kg) undergoing IVF, administer L-arginine 0.5 to 20 g of L-arginine per os daily in three divided doses for the first 2–6 weeks of pregnancy or longer.

Example 2

Improvement of implantation rates after in vitro fertilization with a nitric oxide donor. To a human female (50–90 kg) undergoing IVF, administer nitroglycerine (5–15 mg/day) transdermally for the first 2–6 weeks of pregnancy or longer.

Example 3

Treatment of infertility with a nitric oxide substrate. To a infertile human female (50–90 kg), administer L-arginine 0.5 to 20 g of L-arginine per os daily in three divided doses.

Example 4

Treatment of Infertility with a nitric oxide donor. To a infertile human female (50–90 kg) administer nitroglycerine (5–15 mg/day) transdermally.

Example 5

Improvement of implantation rates after in vitro fertilization with a nitric oxide substrate in combination with progesterone. To a human female (50–90 kg) undergoing IVF, administer nitroglycerine (5–15 mg/day) transdermally in combination with progesterone (Proluton$^R$ Depot (Schering) 250–1000 mg/week i.m.) for the first 2–6 weeks of pregnancy or longer.

Example 6

Treatment of infertility with a nitric oxide substrate in combination with a nitric oxide substrate. To a infertile human female (50–90 kg) administer nitroglycerine (5–15 mg/day) transdermally in combination with L-arginine 0.5 to 20 g of L-arginine per os daily in three divided doses.

Example 7

Improvement of implantation rates after in vitro fertilization with a nitric oxide substrate in combination with progesterone and estradiol. To a human female (50–90 kg) undergoing IVF, administer nitroglycerine (5–15 mg/day) transdermally in combination with progesterone (ProlutonR Depot (Schering) 250–1000 mg/week i.m.) and estradiol valerate 0.5–4 mg/day for the first 2–6 weeks of pregnancy or longer.

Example 8

Postcoital contraception with a nitric oxide synthase inhibitor in combination with an antiprogestin. Administer 0.5–200 mg antiprogestin/day (e.g. mifepristone) in combination with a nitric oxide synthase inhibitor at an effective dose within 72 hours after intercourse.

The preceding examples can be repeated with similar success by substituting the generically or specifically described reactants and/or operating conditions of this invention for those used In the preceding examples.

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent. The preceding preferred specific embodiments are, therefore, to be construed as merely illustrative and not limitative of the remainder of the disclosure in any way whatsoever.

In the foregoing, including the examples, all temperatures are set forth uncorrected in degrees Celsius; and, unless otherwise indicated, all parts and percentages are by weight.

The entire disclosures of all applications, patents and publications, cited above and below, if any, are hereby incorporated by reference.

What is claimed is:

1. A method for improvement of implantation rates in a female mammal after in vitro fertilization which comprises administering to an afflicted female an amount of nitric oxide synthase substrate, a nitric oxide donor, or both, effective to raise the blood level of circulating L-arginine to at least about 50–5000 μmolar above the normally 50–1000 μmolar circulating levels and, optionally, also a progestin or, both of an estrogen and a progestin, in amounts effective to increase the pregnancy rates.

2. The method of claim 1, wherein the mammal is a non-pregnant human female suffering from infertility, or a pregnant female suffering from habitual abortions or a pregnant female exhibiting symptoms of impending abortion.

3. The method of claim 1, wherein the nitric oxide substrate is L-arginine.

4. The method of claim 1, wherein the mammal is a pregnant human female and a nitric oxide donor is administered hereto.

5. The method of claim 4, wherein the nitric oxide donor is sodium nitroprusside, nitroglycerin, SIN-1, isosorbid mononitrate or iso sorbiddinitrate.

6. The method of claim 4, wherein the nitric oxide donor is administered orally.

7. The method of claim 4, wherein the nitric oxide donor is administered transdermally.

8. The method of claim 1, wherein the mammal is a pregnant human female and the nitric oxide substrate or donor is administered thereto in combination with progesterone.

9. The method of claim 1, wherein the mammal is a pregnant human female and the nitric oxide substrate or donor is administered thereto in combination with progesterone and/or estradiol.

10. The method of claim 8, wherein the progestin is progesterone or hydroxyprogesterone caproate.

11. The method of claim 9, wherein the estradiol is estradiol valerate.

12. A method of improving implantation rates and/or pregnancy rates in a female mammal, comprising administering to a female mammal in whom pregnancy is desired an effective amount of (a) a nitric oxide synthase substrate, a nitric oxide donor, or both, optionally in combination with (b) a progestin, and, (c) optionally, in further combination with an estrogen.

13. A method of claim 12, wherein the mammal is a non-pregnant human female suffering from infertility, a pregnant female suffering from habitual abortions, or a pregnant female exhibiting symptoms of impending abortion.

14. A method of claim 12, wherein the nitric oxide synthase substrate is L-arginine.

15. A method of claim 12, wherein the mammal is a pregnant human female and a nitric oxide donor is administered thereto.

16. A method of claim 15, wherein the nitric oxide donor is sodium nitroprusside, nitroglycerin, SIN-1, isosorbid mononitrate or isosorbid dinitrate.

17. A method of claim 15, wherein the nitric oxide donor is administered orally.

18. A method of claim 15, wherein the nitric oxide donor is administered transdermally.

19. A method of claim 12, wherein the mammal is a pregnant human female and a nitric oxide substrate or donor is administered thereto in combination with a progestin.

20. A method of claim 12, wherein the mammal is a pregnant human female and a nitric oxide substrate or donor is administered thereto in combination with a progestin and an estrogen.

21. A method of claim 19, wherein the progestin is progesterone or hydroxy-progesterone caproate.

22. A method of claim 20, wherein the estrogen is estradiol valerate.

23. A method of claim 12, wherein the mammal is a human female and the amount of the nitric oxide synthase substrate, nitric oxide donor or both administered is effective to raise the blood level of circulating L-arginine in said female to at least about 50–5000 $\mu$molar above the normally 50–1000 $\mu$mole circulating levels.

24. A method of claim 12, wherein the mammal is a human female and the amount of the nitric oxide synthase substrate, nitric oxide donor or both administered is effective to raise the nitric oxide donor level to about 1–1000 nmolar.

25. A method of claim 12, wherein the mammal is a human female and the amount of progestin administered is bioequivalent to 50–300 mg of injected progesterone, and the amount of estrogen administered, if any, is bioequivalent to 1–2 mg of estradiol.

26. A method of claim 12, wherein components (a) and (b) are administered sequentially.

27. A method of claim 12, wherein components (a) and (b) are administered simultaneously.

* * * * *